United States Patent [19]

Baker, Jr. et al.

[11] Patent Number: 4,903,699
[45] Date of Patent: Feb. 27, 1990

[54] IMPLANTABLE CARDIAC STIMULATOR WITH AUTOMATIC GAIN CONTROL

[75] Inventors: Ross G. Baker, Jr., Houston; Edward A. Haluska, Angleton; Joseph W. Vandgriff, Freeport, all of Tex.

[73] Assignee: Intermedics, Inc., Angleton, Tex.

[21] Appl. No.: 203,493

[22] Filed: Jun. 7, 1988

[51] Int. Cl.⁴ ............................................. A61N 1/36
[52] U.S. Cl. .......................... 128/419 PG; 128/419 P
[58] Field of Search ............... 128/696, 697, 702, 704, 128/708, 902, 419 PT

[56] References Cited

U.S. PATENT DOCUMENTS

| | | | |
|---|---|---|---|
| 4,000,461 | 12/1976 | Barber et al. | 128/708 |
| 4,312,354 | 1/1982 | Walters | 128/419 PT |
| 4,364,396 | 12/1982 | Barthel | 128/419 PT |
| 4,708,144 | 11/1987 | Hamilton et al. | 128/708 |
| 4,766,902 | 8/1988 | Schroeppel | 128/419 PG |
| 4,768,511 | 9/1988 | DeCote, Jr. | 128/419 PG |

Primary Examiner—Lee S. Cohen
Assistant Examiner—Scott M. Getzow

[57] ABSTRACT

An implantable cardiac stimulator for detecting and treating bradycardias includes a sense amplifier responsive to sensed cardiac signals for detecting cardiac activity. The sense amplifier includes an automatic gain control amplifier, a filter and quad comparator having a pair of signal channels to establish sensing thresholds, margins and signal gain. The sense amplifier has a feedback loop containing a microprocessor which implements preselected algorithms in conjunction with the outputs of the quad comparator to variably adjust the amplifier gain and to programmably control the sensing margin.

3 Claims, 3 Drawing Sheets

QUAD COMPARATOR SECTION

FIG. 4
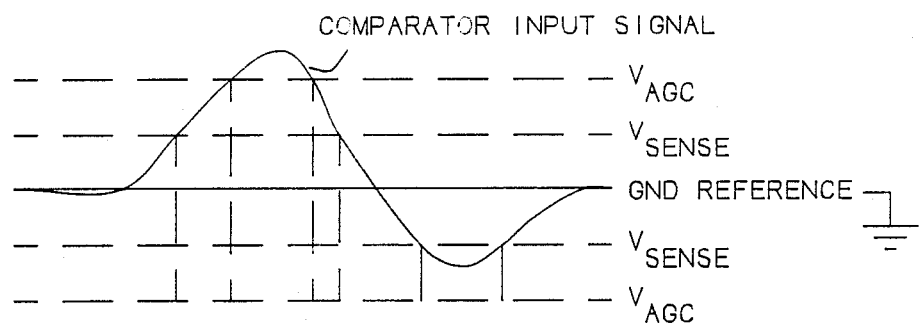
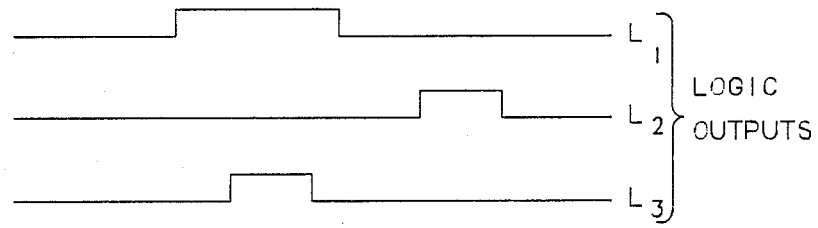
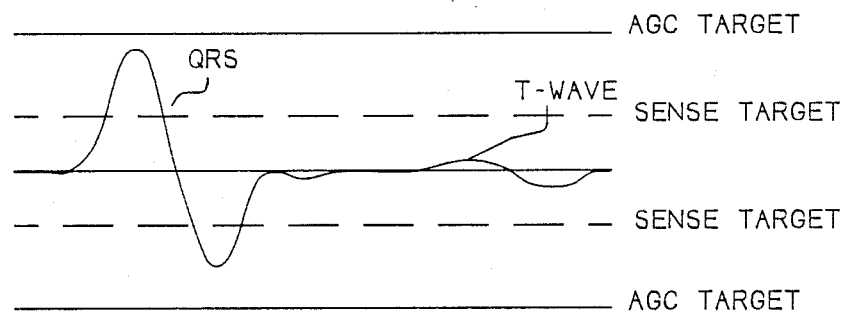
FIG. 5

IMPLANTABLE CARDIAC STIMULATOR WITH AUTOMATIC GAIN CONTROL

FIELD OF THE INVENTION

The present invention relates generally to implantable cardiac stimulators such as pacemakers, and more particularly to automatic gain control suitable for use with either single or dual chamber pacemakers.

Implantation of a cardiac pacemaker has been a typical procedure of choice for treatment of bradycardia patients. The pacemaker pulse generator is implanted in a pouch beneath the skin in the patient's chest and delivers electrical impulses to electrodes positioned at the patient's heart via one or more catheter leads, to stimulate the heart to beat at a desired rate in the normal sinus range.

SUMMARY OF THE INVENTION

According to the present invention, the sense amplifier of the cardiac stimulator is provided with automatic gain control (AGC) as well as bandpass filtering and comparison of sensed signal (sensed event) amplitudes against selected target levels in a system and method for detecting cardiac events. Interactions between gain and pacing are utilized in a manner not found in prior art techniques employed to detect and treat cardiac events.

The AGC amplifier includes an amplifier section having a gain that may be altered as often as necessary to maintain a set of predefined conditions, and a dual set of comparators to convert the processed analog information into digital information to be used by a microprocessor for making decisions about the need for changes in the gain of the amplifier and sensing activity.

BRIEF DESCRIPTION OF THE DRAWINGS

The above and still further objects, features and attendant advantages of the present invention will become apparent from a consideration of the following detailed description of a presently preferred embodiment, taken in conjunction with the accompanying drawings, in which:

FIGS. 4 and 5 are waveforms useful for describing the operation of the sense amplifier according to the presently preferred embodiment.

DETAILED DESCRIPTION OF THE PRESENTLY PREFERRED EMBODIMENT

Figure 1:
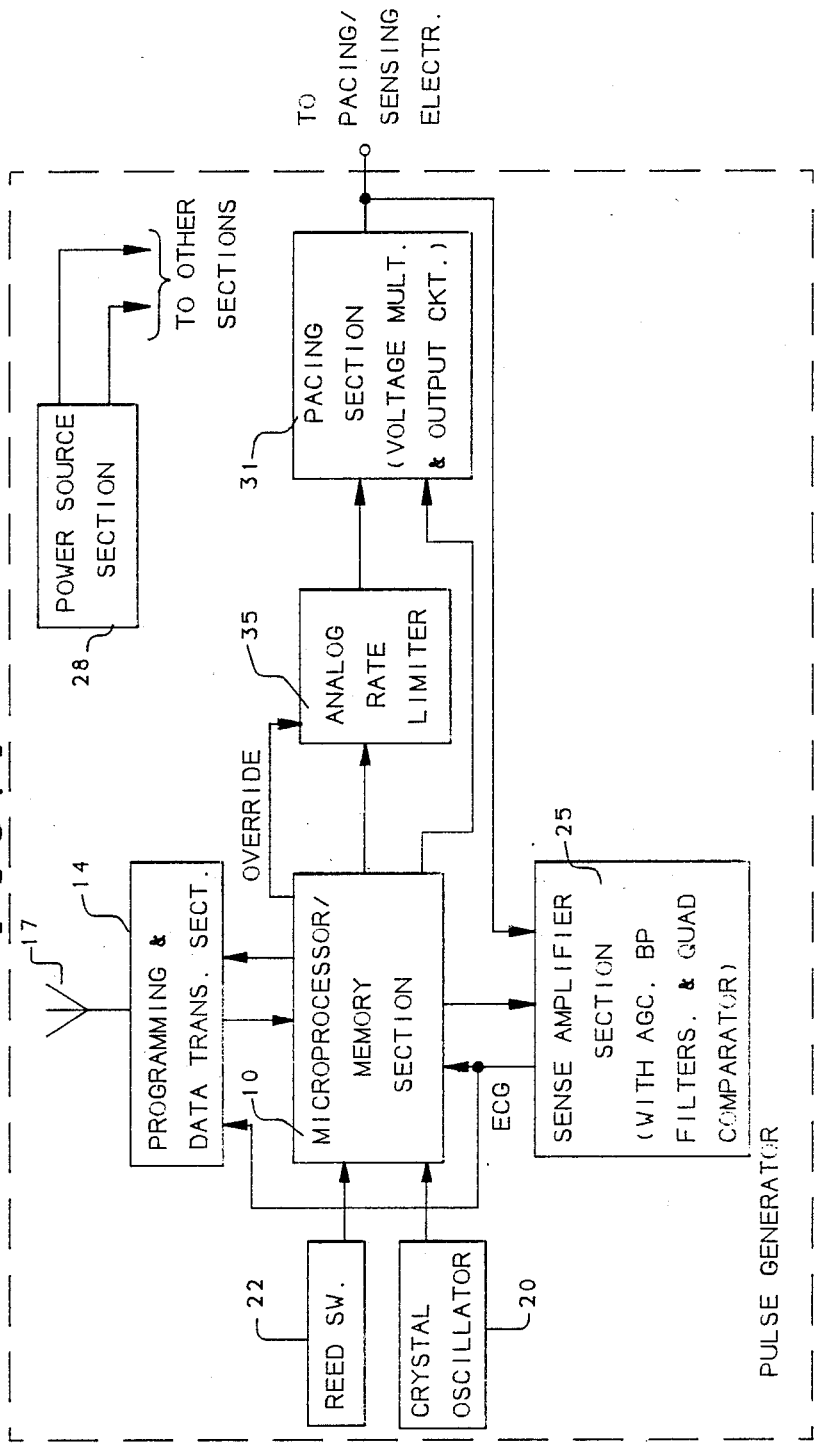
FIG. 1 is a block circuit diagram of the therapy generator of an implantable single chamber cardiac stimulator, utilizing a sense amplifier having AGC according to the presently preferred embodiment.

The block diagram of FIG. 1 is illustrating the circuitry for a single chamber pacemaker. It would only be necessary to create a second channel including a pacing section, analog rate limiter and sense amplifier to form a dual chamber pacemaker employing the subject AGC.

The pulse generator (FIG. 1) unit of the stimulator is adapted to detect preselected aspects of the patient's cardiac activity, and to respond by generating and managing the delivery of pacing therapies. It will be evident, then, that despite its name the pulse generator does more than simply generate pulses in that the generator incorporates circuitry for sensing cardiac activity. Among other things, the generator has a self-contained power source, and is assembled and housed in a metal case which is inert to body tissue and fluids. Lead/electrode assemblies for use in sensing cardiac activity and delivering the pacing impulses to the patient's heart are connectable to the pulse generator. Together, then, the pulse generator and the lead/electrode assemblies constitute the cardiac pacemaker.

The pulse generator includes a digital control section for storing and executing software instructions and for storing and processing the data for all digital functions of the device (aside from those functions which, for purposes of conserving memory capacity, are readily consigned to an external programmer unit). Digital functions of the device may include the physician-programmable aspects, such as provision for programming rate output pulse width, or amplitude and, as well, the various processing, timing, switching, control and other functions which need not be described here inasmuch as they are not essential to an understanding of the present invention.

The pulse generator also includes an analog system portion for functions including those of the present invention involving monitoring of the patient's ECG signal information over each cardiac cycle and enhancing that signal information while reducing noise and other interference through signal filtering and automatic gain control. Other analog functions of the generator include developing the respective impulse waveforms to be delivered for the pacing, transmitting data between the device and external units such as the programmer and transtelephonic monitoring equipment, and protecting against overloads. Also included are the battery cells and voltage regulation and for supplying power to the other sections of the overall pacemaker.

With reference now to FIG. 1, a central microprocessor and associated memory section 10 of the pulse generator processes and stores the data for rates, pulse widths, amplitudes, refractory periods, and other features. Bidirectionally coupled to microprocessor/memory section 10 is a programming and data transmission section 14 for transmitting data to and from the external programmer and/or to receiving and monitoring equipment, via the antenna 17. A crystal oscillator 20 is electrically coupled to section 10 to provide precise timing signals for system operation. A reed switch 22 allows limited external control by means of placing an external magnet (not shown) in proximity to the switch for actuation thereof.

A sense amplifier section 25 of the present invention, described in detail below, is coupled to the microprocessor/memory section 10 to furnish electrogram signal information and to receive control signals from the microprocessor. The sense amplifier also supplies electrogram signal information directly to data transmission section 14 for telemetry to the external monitoring equipment. A quad comparator within sense amplifier 25 serves as the link to convert electrogram, sense signal information from sensing electrode(s) (not shown) attached to the patient's heart into digital information for use by the microprocessor. The microprocessor 10 is disposed in the feedback loop of the sense amplifier 25 for automatic gain control.

The sense amplifier 25 enhances the electrogram signals. Preferably, the sense amplifier 25 has a range of gain of the order of at least 8:1. As will be explained in more detail below, AGC with bandpass filtering is employed to provide the function of reducing the amplitude of signals outside the frequency band of interest.

A pacing section 31 in the pulse generator includes a voltage multiplier and output section (neither of which is shown and both of which are conventional). The multiplier scales up the regulated supply voltage from power source section 28 by multiples of one-half, one, one and one-half, two or three. The output section provides output switching from this scaled voltage to deliver pacing stimuli to the patient's heart via the pacing electrodes (not shown) under the control of the microprocessor 10. An analog rate limit circuit 35 controllably limits the pacing rate, to prevent pacemaker runaway in the event of failure of the crystal oscillator circuit 20. The microprocessor 10 automatically disables the rate limiter 35 whenever high rate pacing pulses are required to be delivered.

Figure 2:
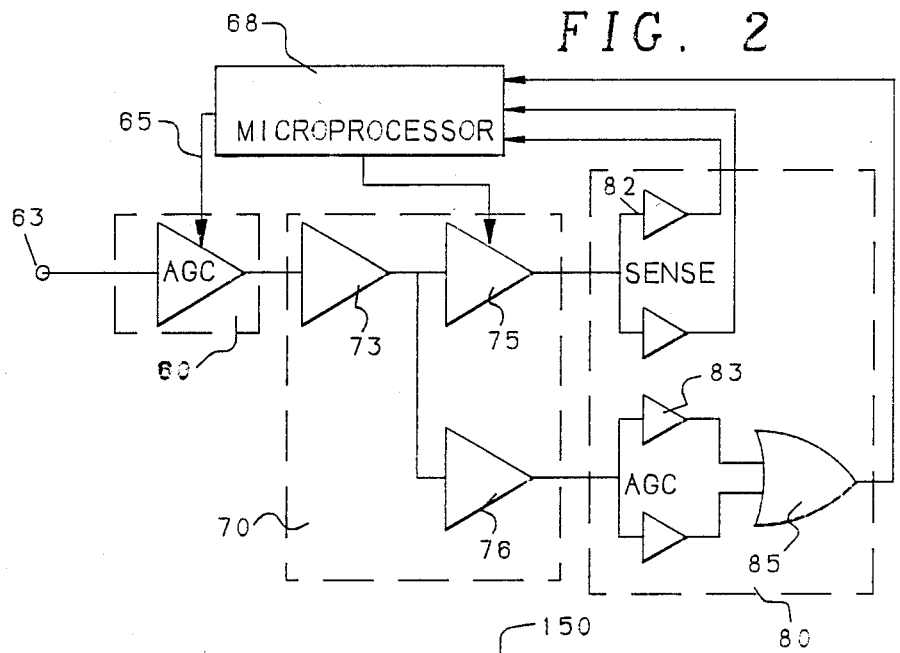
FIG. 2 is a more detailed circuit diagram of the microprocessor and sense amplifier portion of the pulse generator circuit of FIG. 1.

Sense amplifier 25 and its relationship to the microprocessor 10 are illustrated in greater detail in FIG. 2. The ECG waveform components detected by the sensing electrodes (not shown) are applied to an AGC amplifier 60 via an input circuit 63. The gain of amplifier 60 is automatically controlled by a feedback loop 65 containing a portion 68 of the microprocessor/memory section 10 (FIG. 1). The electrogram signals processed by AGC amplifier 60 are further enhanced by a filter section 70 having a primary high gain bandpass amplifier 73 to amplify signals within the band. The output of amplifier 73 is split and applied to separate amplifiers 75 and 76, the former being digitally controlled by microprocessor portion 68. The output derived from amplifier and filter stages 60 and 70 is applied to a quad comparator 80 (to be described in greater detail below with reference to FIG. 3), comprising a set of sensing target comparators 82 and a set of AGC target comparators 83, 85, which develop three inputs to the microprocessor in the feedback loop.

The system of FIG. 2 provides dual signal paths. The signal path through amplifier 75 to the sensing target comparators 82 determines the sensing level and the signal path through amplifier 76 to the AGC target comparators 83 portion is part of the feedback loop that includes the microprocessor 68, which determines the gain of AGC amplifier 60. A sensing margin is defined as the ratio of AGC signal-size at the inputs to sensing target comparators 82 and their respective thresholds sensing. A ratio greater than one must be chosen in order to avoid loss of sensing as a consequence of a reduction in signal amplitude. For example, the use of a 2-to-1 margin would mean that the signal amplitude would have to be reduced by one-half to lose sensing. The goal of the AGC system is to maintain a preset sensing margin. For a given threshold level on the sensing comparator, this may be achieved by adjusting the gain of the AGC amplifier 60 so that the AGC voltage seen by the sensing comparators 82 remains more or less constant. The microprocessor 68 samples the output of the AGC comparators 83 on a cycle by cycle basis. In essence, if the waveform peak (see FIG. 4) exceeds the threshold of the AGC detector the microprocessor 68 will reduce the gain a small amount. If the waveform peak (see FIG. 4) does not exceed the threshold of the AGC detector, the microprocessor will increase the gain a small amount (the increase/decrease decision process will be discussed in more detail later).

The bandpass of the signal path to the sensing comparator is shaped so that frequencies below 25 Hz are attentuated. This gives the desirable effect of attenuating the lower frequency T-wave relative to the QRS complex.

Figure 3:
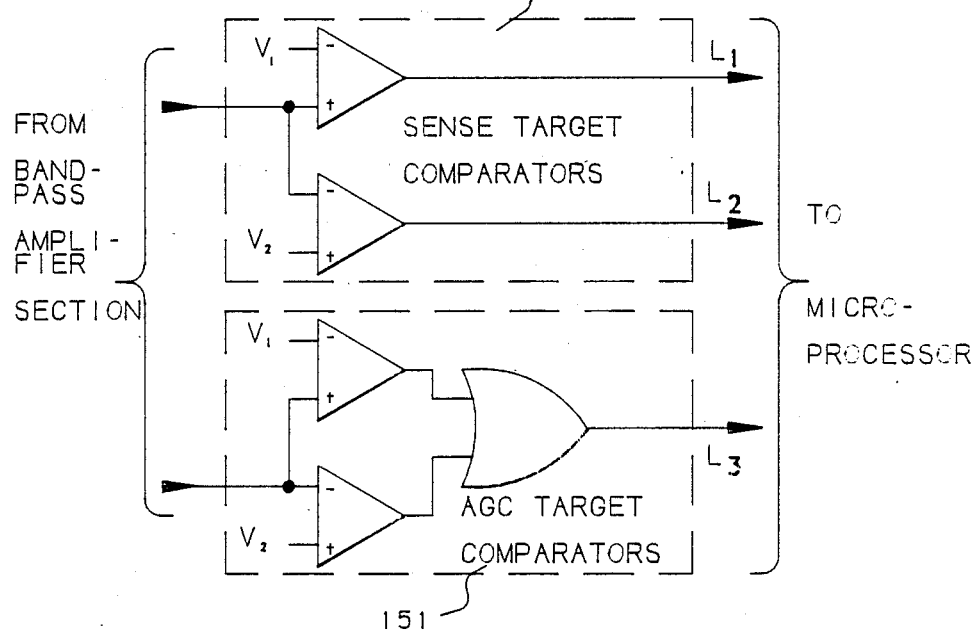
FIG. 3 is a schematic circuit diagram of the quad comparator section of the sense amplifier.

The quad comparator 80 of sense amplifier 25 is shown in FIG. 3, and an exemplary input signal and logic outputs of the comparator are illustrated in FIG. 4. The comparator has two comparator pairs comprising sensing target comparators 150 and AGC target comparators 151. The logic outputs $L_1$ and $L_2$ (upper and lower, respectively) of the sensing target comparators are used by the microprocessor as valid sense input signals. The logical "OR" ($L_3$ either positive or negative) of the AGC target comparators is used by the microprocessor to evaluate the need for increasing or decreasing the AGC amplifier gain. The sensing targets represent a sensing threshold, and the AGC targets represent a sensed signal AGC amplitude target.

By way of an example of operation, in the presence of a QRS complex which is being monitored by the sense amplifier with its sensing and AGC targets, the microprocessor 68 seeks to maintain the gain in such a way that the AGC of the signal in the QRS complex approximately crosses the AGC target, as shown in FIG. 5. Such gain maintenance is achieved in the following manner. Any signal that crosses the sensing targets is considered to be a sense event. If a sense event occurs in a cardiac cycle, then sometime after it is sensed (which may, for example, occur during the refractory period, although the precise time is not significant) a flag is checked which indicates whether or not the AGC target was crossed by that sense event. If the AGC target was crossed, (referred to as sensing a 'high') it is an indication that the gain is too high and should be decreased. If this occurs repetitively, the microprocessor decreases the gain. In the presently preferred embodiment, the gain is decreased by a certain percentage. As an alternative, however, the gain may be decreased by a fixed amount.

The microprocessor also counts cycles in which sense events have occurred but there has been no crossing of the AGC target (referred to as sensing a 'low'). If this occurs predominantly the microprocessor recognizes that the gain is too low and must be increased. Here again, the increase may be effected as a fixed percentage or a fixed amount. That is, the microprocessor has means for adjusting gain in accordance with a specific algorithm which requires sensing of two lows in a row, i.e. two consecutive sensed events which exceed the sense level but not the AGC level, in order to increase gain or sensing one high, i.e. a sensed event which exceeds the AGC level, to decrease gain.

With the above considerations in mind, the following AGC algorithms are implemented in the presently preferred embodiment of the invention (independently implemented for each chamber of dual chamber pacemaker):

1. The microprocessor uses a counter to accumulate comparator target crossings.

2. The counter is initialized to its middle value, 128. For any specific sensed cardiac event, if both the sense and AGC comparator targets are crossed, (that is, a high is sensed) the counter is incremented by two. If only the sense comparator target is crossed, (that is, a low is sensed) the counter is decremented by one. As sensed events are accumulated in the counter, if the counter overflows, the AGC gain is reduced by one step and the counter is reset to its middle value. If the counter underflows, the AGC gain is increased by one step and the counter is reset to its middle value. These values are representative, but the important fact is that incrementing is weighted more heavily than decrementing to bias towards gain reduction and prevent double sensing due to T-waves.

3. When the microprocessor detects noise the counter is reset to its middle value. This prevents noise signals from affecting the AGC gain.

4. In the special case of nearly 100% pacing where the intrinsic cardiac activity is less than the programmed pacing rate, the counter is caused to drift toward its middle value. Another counter accumulates cycle of pacemaker activity. Every 256 pacemaker cycles; if the AGC accumulator counter is greater than 128, it is decremented by one. If it is less than 128, it is incremented by one. This prevents occasional spurious events detected over long periods of time from causing changes in gain.

What is claimed is:

1. An implantable cardiac stimulator for detecting cardiac cycles by analyzing electrical signals produced by the heart, comprising:

means for detecting electrical signals produced by the heart; and amplifier means responsive to the detected signals and having dual signal paths for said detected signals, one of said paths having a feedback loop with means for automatically adjusting the gain of the amplifier means, the other said signal paths enables the determination of a sensing level, said means for automatically controlling the gain including an algorithm controlling gain requiring a ratio of greater than 1 to 1, said algorithm controlling gain requiring sensing of two lows in a row to increase gain and sensing one high to decrease gain whereby the gain and threshold relationships between said dual signal paths maybe altered to produce variable sensing margins.

2. An implantable cardiac stimulator according to claim 1, wherein said ratio is 2:1.

3. An implantable cardiac stimulator according to claim 1, wherein the algorithm controlling gain avoids over-amplification when no valid signal is present, for purpose of noise immunity, and appropriate sensing when signals return.

* * * * *